United States Patent
Guracar et al.

(10) Patent No.: US 12,102,475 B2
(45) Date of Patent: Oct. 1, 2024

(54) IMAGE CLASSIFICATION-DEPENDENT USER INTERFACE IN ULTRASOUND IMAGING

(71) Applicant: Siemens Medical Solutions USA, Inc., Malvern, PA (US)

(72) Inventors: Ismayil M. Guracar, Redwood City, CA (US); Bimba Rao, San Jose, CA (US); Cynthia Wolverton, Mountain View, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 52 days.

(21) Appl. No.: 16/946,541

(22) Filed: Jun. 26, 2020

(65) Prior Publication Data

US 2021/0401405 A1  Dec. 30, 2021

(51) Int. Cl.
| | |
|---|---|
| *A61B 8/08* | (2006.01) |
| *A61B 8/00* | (2006.01) |
| *G06F 18/24* | (2023.01) |
| *G06N 3/08* | (2023.01) |
| *G06V 10/25* | (2022.01) |
| *G06V 10/82* | (2022.01) |

(52) U.S. Cl.
CPC ............ *A61B 8/0883* (2013.01); *A61B 8/461* (2013.01); *A61B 8/469* (2013.01); *A61B 8/488* (2013.01); *A61B 8/5207* (2013.01); *G06F 18/24* (2023.01); *G06N 3/08* (2013.01); *G06V 10/25* (2022.01); *G06V 10/82* (2022.01)

(58) Field of Classification Search
CPC ........ A61B 8/5215–5223; A61B 8/465; A61B 8/469; A61B 8/0883; A61B 8/488
See application file for complete search history.

(56) References Cited

U.S. PATENT DOCUMENTS

| | | |
|---|---|---|
| 7,221,972 B2 | 5/2007 | Jackson |
| 9,408,587 B2 | 8/2016 | Pelissier |
| 2002/0173721 A1 | 11/2002 | Grunwald et al. |
| 2003/0013959 A1* | 1/2003 | Grunwald ........... G01S 15/8981 600/437 |
| 2005/0049506 A1* | 3/2005 | Jackson .................. A61B 8/00 600/455 |

(Continued)

FOREIGN PATENT DOCUMENTS

| | | |
|---|---|---|
| CN | 201361044 | 12/2009 |
| CN | 101842718 | 9/2010 |

(Continued)

OTHER PUBLICATIONS

<https://pep.siemens-info.com/en-us/sequoia-control-panel-3d-4d>, (Jan. 15, 2019). (Year: 2019).*

(Continued)

*Primary Examiner* — Joel Lamprecht
*Assistant Examiner* — Ashish S Jasani (57) ABSTRACT

For a classification-dependent user interface in ultrasound imaging with an ultrasound scanner, the ultrasound scanner classifies a view represented in an image. The user interface changes according to the view, allowing one or a few user inputs to be used for different user options or behavior combinations appropriate for the classified anatomy. The context from imaging alters the behavior of a given user input element of the user interface.

19 Claims, 4 Drawing Sheets

(56) References Cited

U.S. PATENT DOCUMENTS

| | | | |
|---|---|---|---|
| 2008/0072151 A1* | 3/2008 | Song | G06F 3/0481 |
| | | | 715/708 |
| 2009/0254848 A1 | 2/2009 | Glaser-Seidnitzer et al. | |
| 2009/0088640 A1* | 4/2009 | Park | G06K 9/6292 |
| | | | 707/E17.046 |
| 2010/0191120 A1* | 7/2010 | Kraus | A61B 8/467 |
| | | | 600/459 |
| 2011/0161862 A1 | 6/2011 | Hibi et al. | |
| 2011/0262018 A1* | 10/2011 | Kumar | G06T 7/0012 |
| | | | 382/131 |
| 2012/0014588 A1* | 1/2012 | Chono | A61B 8/00 |
| | | | 382/133 |
| 2012/0157843 A1 | 6/2012 | Lavin et al. | |
| 2013/0137989 A1 | 5/2013 | Chen et al. | |
| 2014/0004834 A1 | 1/2014 | Mian et al. | |
| 2014/0052001 A1 | 2/2014 | Ionasec et al. | |
| 2014/0081139 A1 | 3/2014 | Zhang et al. | |
| 2014/0177935 A1* | 6/2014 | Nair | A61B 8/445 |
| | | | 382/132 |
| 2016/0220231 A1* | 8/2016 | Lee | A61B 8/488 |
| 2016/0354060 A1 | 12/2016 | Perrey et al. | |
| 2017/0086780 A1* | 3/2017 | Sokulin | A61B 8/5207 |
| 2017/0300205 A1* | 10/2017 | Villa | G06F 3/04886 |
| 2017/0319283 A1 | 11/2017 | Suresh et al. | |
| 2018/0055485 A1* | 3/2018 | Lalena | A61B 8/461 |
| 2018/0206819 A1* | 7/2018 | Saarinen | A61B 8/0866 |
| 2018/0228473 A1* | 8/2018 | Cho | A61B 8/54 |
| 2018/0368812 A1* | 12/2018 | Kim | A61B 8/488 |
| 2019/0139218 A1 | 5/2019 | Song et al. | |
| 2019/0148011 A1* | 5/2019 | Rao | G16H 30/40 |
| | | | 600/437 |
| 2019/0261956 A1* | 8/2019 | Srinivasan | G06V 10/20 |

FOREIGN PATENT DOCUMENTS

| | | |
|---|---|---|
| CN | 102414575 | 4/2012 |
| CN | 104380248 | 2/2015 |
| CN | 104648407 | 5/2015 |
| CN | 105877779 | 8/2016 |
| CN | 105899143 | 8/2016 |
| CN | 106073826 | 11/2016 |
| CN | 107847745 | 3/2018 |
| CN | 108714034 | 10/2018 |
| CN | 108938002 | 12/2018 |
| CN | 109758178 | 5/2019 |
| CN | 110832441 | 2/2020 |
| CN | 111026300 | 4/2020 |
| CN | 111053573 | 4/2020 |
| JP | 2013027497 | 2/2013 |
| JP | 2016209407 | 12/2016 |
| WO | WO2018002776 A1 | 1/2018 |

OTHER PUBLICATIONS

Chono, Tomoaki, "Automation technology for cardiac function measurements on the LISENDO 880," retrieved from https://hce.fujifilm.com/fileadmin/hitachi-medical-eu/ultrasound_preview/cardiovascular/downloads/MEDIX_Report_Automation_technology_for_cardiac_function_in_LISENDO_880.pdf on Jul. 13, 2021.

* cited by examiner

FIG. 7

IMAGE CLASSIFICATION-DEPENDENT USER INTERFACE IN ULTRASOUND IMAGING

BACKGROUND

The present embodiments relate to ultrasound imaging. In ultrasound imaging, the sonographer controls the scanning using various user inputs. This may require the sonographer to perform repetitive motions and/or to reposition their hand to accomplish workflow tasks in control of the imaging the patient. There is a need for an improved user interface which minimizes the manual effort required to accomplish workflow tasks.

Some ultrasound scanners have a user interface area that allows many functions to be performed without moving the hand. For example, a trackball is surrounded by three or four labeled function keys, allowing the user to control a cursor or pointer as well as perform basic functions such as update, position, and size. This user interface area may minimize motion but has a limited number of function keys. Performing other workflow tasks often requires use of other keys spaced from the trackball user interface area.

SUMMARY

By way of introduction, the preferred embodiments described below include methods, computer readable storage media, instructions, and systems for a classification-dependent user interface in ultrasound imaging with an ultrasound scanner. The ultrasound scanner classifies a view represented in an image. The user interface changes according to the view, allowing one or a few user inputs to be used for different user options or behavior combinations appropriate for the classified anatomy. The context from imaging alters the behavior of a given user input element of the user interface.

In a first aspect, a method is provided for a classification-dependent user interface in ultrasound imaging with an ultrasound scanner. The ultrasound scanner scans a patient and classifies content of an image from the scanning. Anatomy selection options are assigned to a user input element of the user interface. The anatomy selection options are assigned based on the classified content. A Doppler gate or region of interest for flow imaging is placed in response to user input with the user input element. The user input selects anatomy using the anatomy selection options as assigned based on the classified content. Flow is imaged with the Doppler gate or region of interest as placed.

In a second aspect, a method is provided for a classification-dependent user interface in ultrasound imaging with an ultrasound scanner. The ultrasound scanner scans a cardiac region of a patient. The ultrasound scanner identifies a cardiac view in an image from the scanning. A list of anatomical locations of the identified cardiac view is assigned to a single user input of the ultrasound scanner. One of the anatomical locations is selected in response to operation of the single user input. Flow imaging at the selected one of the anatomical locations is performed.

In a third aspect, a system is provided for an image classification-dependent user interface in ultrasound imaging. An image processor is configured to classify anatomy represented in ultrasound data, alter behavior of a user interface component based the classification of the anatomy such that different classification provides for different behavior of the same user interface component, and receive selection of an anatomy area using the user interface component with the behavior for the classification. An ultrasound system is configured to image based on the selection of the anatomy area.

The present invention is defined by the following claims, and nothing in this section should be taken as limitations on those claims. Further aspects and advantages of the invention are disclosed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An ultrasound scanner includes an image classification-dependent user interface. Based on the live classification of one or more displayed or non-displayed images, the function of user interface elements is directed to specific behavior to achieve desired workflow actions with minimal hand motion. For example, a button in a homebase area (e.g., trackball and immediately surrounding buttons) is assigned different anatomical references for flow imaging based on the anatomical content determined from classification. One or more user interface elements behave in a way that changes with image anatomy classification content.

In a flow imaging example, the user interface element behaves to select different color region-of-interest (ROI), placement options based on classification of the anatomy represented in an image. Different image views result in the same user interface elements being associated with different selectable anatomy. The anatomy area for color ROI placement is selected using the programmed behavior. In another flow imaging example, the user interface element enables selecting the anatomy area for Doppler gate placement. The Doppler gate is placed in response to the user-accepted, prior color Doppler ROI placement. Anatomy within or around the ROI may be detected and used in placing the Doppler gate. The user interface element is assigned behavior based on classification of the image content, which behavior is used to place the ROI. The ROI is used to position the Doppler gate. Alternatively, the behavior of the user interface element is set to cycle through different Doppler gate locations based on the classification of the image anatomical content.

In one embodiment, a single button, softkey, command word, or other user interface element is assigned content-based behavior. A list of anatomy associated with the content is linked to the single user interface element. Activation of that element cycles or advances through the sequence of anatomy (e.g., possible ROI or gate locations). One touch or voice-initiated advancement within the sequence of anatomy areas is provided as the behavior. Different content being recognized alters the behavior of the single user interface element by using a different list of anatomical area options. A single keystroke may select a desired color ROI and/or pulsed wave (PW) gate placement from a list of anatomy area possibilities, which possibilities depend on the view being scanned.

The examples below use ultrasound imaging of a cardiac region of a patient. For example, four standard views are provided for cardiac imaging—apical four chamber, apical two chamber, parasternal long axis, and parasternal short axis. Image classification is used to recognize the view. Based on the recognition of a particular view, the behavior of a user interface element is set. Different views correspond to different behavior (e.g., different possible anatomical-related ROI or gate locations and/or corresponding priority in the list). In other embodiments, other behaviors than an ordered list, other types or regions of imaging than cardiac, and/or other views than the four standard views are provided. For example, the ultrasound system classifies a view relative to a fetus or particular anatomy in the view. The user interface element is then programmed to provide workflow operations associated with that particular anatomy or view.

Figure 1:
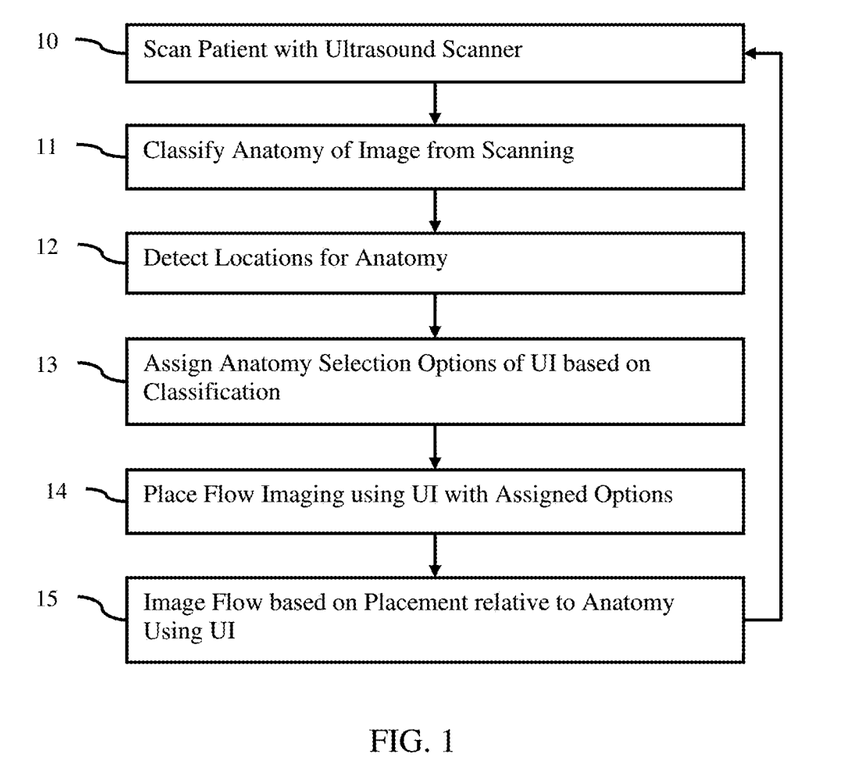
FIG. 1 is a flow chart diagram of one embodiment of a method for a classification-dependent user interface in ultrasound imaging with an ultrasound scanner.

FIG. 1 shows one embodiment of a method for a classification-dependent user interface in ultrasound imaging with an ultrasound scanner. The ultrasound scanner identifies the view or other anatomical content represented by ultrasound data as a classification. The classification is used to alter operation of one or more user interface elements, such as assigning a list of anatomy-related placements of ROIs and/or Doppler gates to a single user interface element where different lists are used for different classes.

Figure 7:
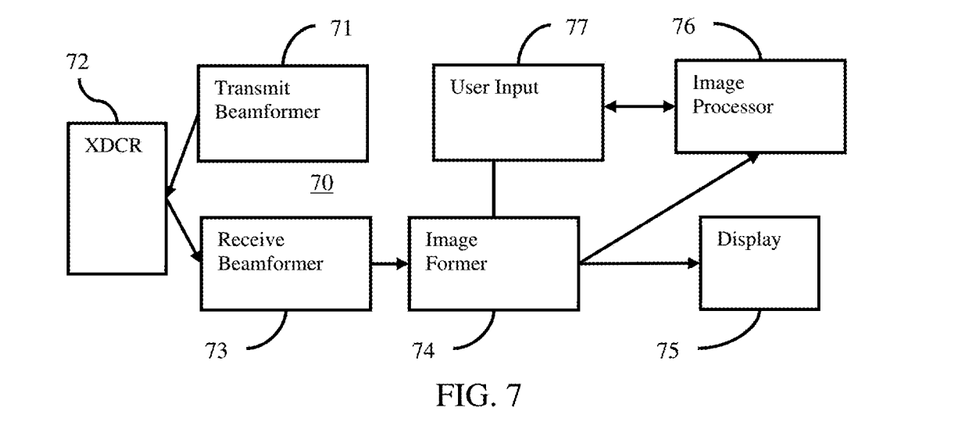
FIG. 7 is a block diagram of one embodiment of a system for a classification-dependent user interface in ultrasound imaging.

The method is performed by the system shown in FIG. 7 or a different system. For example, a medical diagnostic ultrasound imaging system scans in act 10 and images in act 15. An image processor classifies in act 11, detects in act 12, assigns in act 13, and places in act 14. A user interface, such as a button or key, is used with or by the image processor for the assigning of act 13 and the placement of act 14. A display is used for imaging in act 15. The display may be used to show the user placement in act 14.

The acts are performed in the order shown (i.e., top to bottom or numerical) or another order. For example, act 12 is performed as part of act 11 or performed before act 11 to assist in classification. As another example, act 12 is performed after the assignment of act 13.

Additional, different or fewer acts may be used. For example, acts for configuring the ultrasound scanner to perform imaging are included. As another example, acts for the review or another use of the image are performed. In yet another example, act 15 is not performed.

In act 10, the ultrasound scanner scans a patient. For example, the ultrasound scanner scans a cardiac region (e.g., heart). Acoustic energy is transmitted, and echoes are received. Any type and/or format of scanning is provided. For example, a B-mode scan is performed. B-mode frames of data are generated by B-mode scanning. A B-mode image represents the intensity or strength of return of acoustic echoes. Other types of detection and corresponding scans are performed. For example, color flow (e.g., flow-mode) estimation is used. Velocity, power, and/or variance as a function of location are estimated. As another example, harmonic mode is used, such as imaging at a second harmonic of a fundamental transmit frequency. Combinations of modes may be used. In yet another example, a Doppler or PW mode is used, such as for spectral imaging.

The scanning is to acquire a frame of data representing the patient at a given period or time. In other embodiments, the scanning is on-going. A sequence of frames of data are acquired over time. The frames of data are in a scan format, such as a polar coordinate format. Alternatively, the frames of data are scan converted into a display format, such as a Cartesian coordinate format. The ultrasound data is data after or before beamformation, detection, filtering, scan conversion, display color mapping, or display. An ultrasound image may be a frame of data that may be used for imaging (e.g., beamformed or detected data prior to scan conversion) or has been used for imaging (i.e., displayed or formatted for display).

In act 11, the ultrasound scanner classifies the content of an image. A frame of ultrasound data or another image representing the patient is classified. The classification occurs in real-time, such as before the ultrasound scanner completes acquisition and/or generation of another image and/or within 1 or 2 seconds of having acquired the frame of ultrasound data. Alternatively, the classification is performed off-line or not in real-time.

The classification identifies a view or anatomical content. In the cardiac imaging example, the classification identifies the image as represented an apical four chamber, an apical two chamber, a parasternal long axis, or a parasternal short axis view. In other examples, the classification identifies the image as representing a given organ or region of the body, such as classifies the ultrasound data as representing the heart.

Any classification may be used. For example, pattern or template matching is used. The template that best matches the distribution of ultrasound data is labeled. The label is the classification. As another example, a machine-learned model, such as a neural network, classifies. The ultrasound data is input to the machine-learned model, which outputs the classification in response. Other image processing may be used for classification.

The classification provides information about what is represented in the image. This information may be used to adapt the user interface. Rather than requiring user input or indication by what imaging application is selected and further combinations of inputs to establish the desired workflow, the ultrasound scanner identifies the anatomical content and uses the information to program the user interface.

In act 12, the ultrasound scanner detects locations of features of the content. As part of classification or post-classification, one or more landmarks, organs, or other locations are detected. For example, valve, vein, vessel, artery, heart wall, and/or other cardiac structures are detected. The location or locations within the region (e.g., field of view (FOV)) represented by the ultrasound data for one or more features are determined.

The features to be detected and/or the detectors to use for detection may be selected based on the classification. Alternatively, detectors are applied regardless of the classification. The features may be used to find different anatomical regions (areas) that make up the anatomical content represented in the frame of ultrasound data.

Any detector may be used. For example, region-growing, skeletonization, and/or other image processing is used. As another example, template matching is performed. In yet another example, a machine-learned model or models are applied.

In act 13, the ultrasound scanner (e.g., image processor) assigns behavior to the user interface element based on the classification. For example, the anatomy selection options are assigned to a user input element of the user interface.

The user interface includes one or more user input devices. For example, the user interface includes one or more buttons or keys, sliders, rotating knobs, touch pads, track ball, mouse, and/or touch screen. The buttons or keys may be part of a keyboard or separate from a keyboard. In one embodiment, a user control console includes a trackball with one or more buttons surrounding or adjacent to the trackball. These buttons may be labeled for particular purposes, such as update, enter/select, position, and/or size. The buttons are against or adjacent to the trackball. Other buttons are spaced further from the trackball. A voice command word may be used as the user interface element.

The function or behavior of one or more user interface elements (e.g., entry or control device) is assigned. The behavior may or may not match the labeled function. One or more workflow options are linked to the user interface element. For example, a list of anatomy is linked. The user interface element is assigned to cycle through the list in an order. Anatomy selection options are assigned to the user interface element. In other embodiments, other options than anatomy selection options are linked. For example, options to activate, alter type of detection, change filtering, adjust amplification, and/or other steps in a workflow implemented by the ultrasound scanner are linked. Any of various behaviors may be linked.

In one embodiment, the assignment is for a single one of the user interface elements. For example, one button (e.g., "update" button) is assigned the anatomy selection options. By depressing that button, different anatomy options are provided for selection. The order of presentation for selection (i.e., the order of anatomy presented as well as which anatomy) is used to link input using the user interface element to operation of the ultrasound scanner.

The anatomy selection options or other options are assigned based on the classified content. In the anatomy selection options embodiment, the classified content identifies a list of anatomy viewable or represented in the image. Different anatomical content (i.e., different classification) results in different lists of anatomy for selection. The different anatomy likely to be of interest for a given view is included in the list for selection by the user. The behavior (e.g., list of options) changes for the user interface element based on the content.

The list includes the locations of the features in the image. Based on the classification in act 11 and/or detection in act 12, a list of anatomical selection options for anatomy or features (e.g., landmarks) represented in the ultrasound data is assigned to the user interface element. In the cardiac example, an ordered list of anatomical locations in the identified cardiac view are assigned to one or more user interface elements, such as assigning the list to a single user input (e.g., "update" button). The list of anatomy areas is dependent on the actual acquired image contents determined by automatic view classification.

The classification in act 11 and the assignment of act 13 occur in real-time with the scanning of act 10. As imaging continues, the classification and assignment also continue. The assignment may be updated where the content changes. Where the content continues to be the same as confirmed by the last classification, the assignment stays the same. Within 1 or 2 seconds of completion of acquisition or image generation of a current frame of data and/or before formation of the next image or frame of ultrasound data, the classification is repeated, and the assignment is confirmed or altered. For example, the assignment occurs based on the view classifier after (or before) entry into color or pulse wave (PW) modes.

Figure 2A:
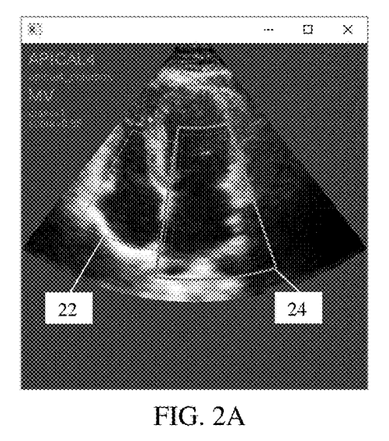
FIGS. 2A and 2B illustrate example ROI locations available based on classification of a view as apical four chamber.
Figure 2B:
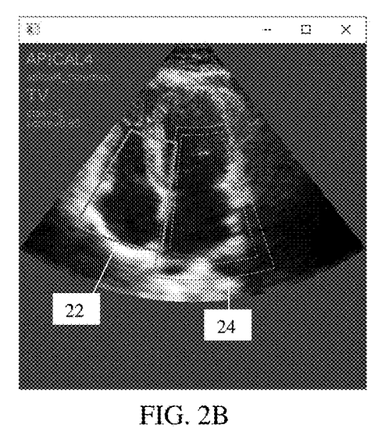

FIGS. 2A and 2B show an example. The classification of the image of FIGS. 2A and 2B is apical four chamber view. Based on this classification, two anatomical regions or areas 22, 24 are assigned to a button (e.g., "update" button on a control console). These two areas 22, 24 represent areas that may be of interest in this view. The areas 22, 24 are regions of interest (ROIs) fitting around, over, or within detected anatomy. For example, the areas 22, 24 are color ROIs. The classification causes the assignment of these two ROIs 22, 24 to the user interface element, then allowing the user to select the anatomy of interest for this scan of this patient.

The user input or interface element may be a button, such as a key. In one embodiment, one of the "generic" keys (e.g., "update" button) adjacent to a trackball or other cursor control is used. In other embodiments, a button on a transducer (e.g., a multi-function "+" key on the transducer) is used. By operating the button, the selection options assigned to the element are cycled.

In another embodiment, the user input or interface element is a softkey or region of a touch screen. A graphical representation of the anatomy selection options assigned based on the classified content is generated. A touch screen area displays ROI placement anatomy area choices. A heart representation, such as a heart icon or icons of different anatomy forming a cartoon, wire frame, or graphical representation of the content of the image may be used. In another embodiment, a live actual cardiac image with areas highlighted is used. The touch screen user interface element shows and receives selection of the different detected anatomy options appropriate for the classified view.

Figure 6:
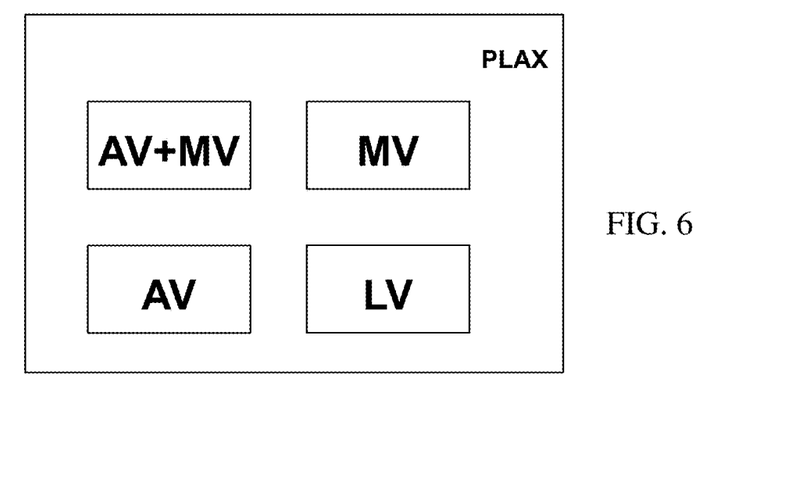
FIG. 6 illustrates example graphics for selection of anatomy locations.

FIG. 6 shows an example. The classification indicates a parasternal long axis view, so a list of anatomy options for that view are presented. The list includes the mitral valve, the apical valve, the left ventricle, and a combination of the apical valve and the mitral valve. Where the classification is the apical four chamber view, the options displayed may be tricuspid valve and mitral valve. Additional, different, or fewer anatomical locations may be included in the lists of anatomical locations of these examples. Other views may have other lists.

In another embodiment, the user interface element is a voice activation term. For example, the word "next" or "update" is assigned to the list of anatomical selection options. The user utters the word "next" or "update," and, depending on the context, the system provides varying behavior (e.g., different anatomical selection options or order). The voice activation is provided with image class dependent context. In one embodiment, B-mode imaging is performed. The view is classified as one of the standard cardiac views. The user utters "color," which places an ROI at a first anatomy area of the options. If in a color imaging mode, uttering "color" may exit the color mode. If in a PW mode, uttering "color" may enter the color mode. Similarly, uttering PW or Doppler may place a gate at the first anatomical location in the list if in B-mode, exit color and enter PW mode if in color mode, or exit PW mode if in PW mode. Uttering "next" or "update" in B-mode may provide no action or may place a color ROI without activating color mode. Uttering "next" or "update" in color or PW modes may move the ROI or gate, respectively, to the next anatomy option on the list, allowing the user to operate the one user interface element to cycle through various anatomical options for ROI or gate placement associated with the view as classified. Other command words and/or actions may be used.

The standard views may depend on the type of ultrasound imaging and/or transducer, such as trans-thoracic echo, trans-esophageal, and intra cardiac echo. Standard views for trans-thoracic echo include Apical2, Apical3, Apical4, Apical5, Parasternal Long Axis, Parasternal Long Axis Right Ventricular Inflow Tract, Parasternal Long Axis Right Ventricular Outflow Tract, Parasternal Short Axis Aortic Valve, Parasternal Short Axis Left Ventricle, Parasternal Short Axis Mitral Valve, Subcostal Four Chamber, Subcostal Inferior Vena Cava, and Suprasternal. Standard views for trans-esophageal include Mid-Esophageal (ME) views, such as ME 2 Chamber, ME 4 Chamber, ME_AOV_SAX, ME_LAA, and ME_LAX. Standard views for intra cardiac echo may include Left Atrium, Left Atrial Appendage, Left Inferior Pulmonary Vein, Right Inferior Pulmonary Vein, Left Superior Pulmonary Vein, Right Superior Pulmonary Vein, Esophagus, and Interatrial Septum. In non-cardiac examples, standard views may include Left Kidney longitudinal, Left Kidney short axis, Right Kidney, and Liver.

In act 14 of FIG. 1, the image processor or ultrasound scanner operates based on user input with the assigned user interface element. In the anatomical selection options embodiment, the image processor places an ROI or PW gate based on operation of the user interface element. Subsequent operation cycles through the list of anatomical options.

In one embodiment, the assigned behavior includes turning on flow imaging (e.g., color or flow mode representing spatial distribution of velocity, energy, and/or variance or PW or Doppler mode representing spectral information at a gate). The use or operation of the user interface element turns on flow imaging as well as places the ROI or gate within the B-mode image. The user input selects the anatomy of interest for flow imaging and activates the flow imaging. The anatomy of interest is selected from the options based on the classified content. By repeating user input or operation of the user interface element, the anatomy of interest for the flow imaging shifts or changes to the next ROI or gate location on the list. A flow region of interest for the flow imaging is cycled through the anatomy list in response to use of the user input element (e.g., operation of the button). For example, the "update" key cycles through a set of anatomy areas for targeting automatic ROI placement. The sequence depends on the view classifier result. If the view classifier sees a new view, then the anatomy area sequence is reset or returns to a previously stored state for the given anatomy The ROI is a scan region within a field of view (FOV). For example, the ROI is a sub-set of the FOV. The ROI is shaped based on the scan line distribution. For linear scans, the scan lines are parallel. The resulting ROI is a square or rectangular box. For sector or Vector® scans, the scan lines diverge from a point on the transducer face or a virtual point positioned behind the transducer, respectively. The sector and Vector scan formats of scan lines scan in a fan shaped ROI. The Vector scan may be a fan shaped region without the origin point included, such as resembling a trapezoid (e.g., truncated triangle). Other shapes of ROIs may be used, such as square or rectangular in a sector or Vector® scan.

The orientation may also be determined to include or avoid certain locations. The orientation may be based on the limits on steering from a transducer, detected landmarks that may cause acoustic shadowing, and/or directivity response of the tissue being quantified.

The ROI has a default size. The ROI is any size, such as 3 cm in lateral and 5 cm in axial. For flow imaging, the ROI is sized to avoid tissue locations. The size may be based on the locations of detected anatomy, fitting the ROI to the patient.

For a PW gate, the gate is sized and positioned to be in the flow of interest. For example, the PW gate is placed over a valve, in the inflow tract of the valve, or in the outflow tract of a valve. The PW gate is a point or region (e.g., includes one or more beamformer sample locations) where the measurements are combined for Fourier transformation to generate a spectrum representing energy as a function of frequency or velocity at a given period or time.

By operating the user input element, the assigned behavior is activated. In the embodiment of FIG. 1, the assigned behavior is the list of anatomy selection options. For example, one of the anatomical locations is selected in response to operation of the single user input. By operating the single user input again, the next anatomical location in the list of options based on the classification is selected and the corresponding flow region placed based on the selection. The user may cycle through the list in response to repetitive operation of the single button. The list of anatomy areas is dependent on the actual acquired image contents determined by automatic view classification. Initial entry to color or PW mode will pick the first anatomical area in the sequence based on view. Subsequent activation or use of the user interface element selects the next anatomical area. For example, each press of the update key initiates inference (i.e., classification) and ROI placement, cycling to the next anatomy area target.

FIGS. 2A and 2B show one example. The classification identifies the view as an apical four chamber view. The first anatomical region on the list assigned to the user interface element for this view is an ROI 24 around the mitral valve. When the user operates the user interface element, the ROI 24 is positioned by the image processor based on the detection, and color or flow mode is activated for imaging flow in the ROI 24 (see FIG. 2A). If the user operates the user interface element again, the ROI 24 is shifted to the ROI 22 for color or flow imaging of the tricuspid valve (see FIG. 2B). Operation again would shift to the next anatomical selection option in the assigned list. For example, operation again shifts back to the ROI 24.

Figure 3:
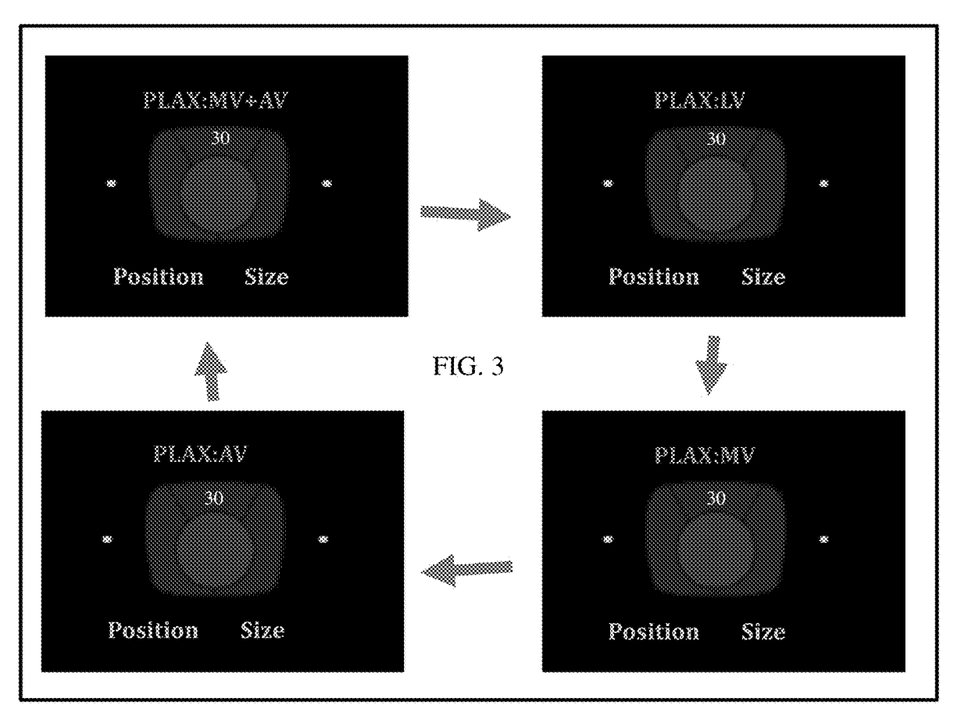
FIG. 3 illustrates an example of cycling through different anatomical locations for a parasternal long axis view.

FIG. 3 shows an example from the user interface perspective. A track ball with three adjacent buttons is represented. The upper button 30 is an "update" button but may have a different label. The view is classified as the parasternal long axis view. The initial anatomical region for color or flow-mode imaging is an ROI for imaging flow at both the mitral and atrial valves. Activating the button 30 causes the ROI to change to the left ventricle. Activating the button 30 again causes the ROI to change to the mitral valve. Activating the button 30 yet again causes the ROI to change to the atrial valve. Activating the button 30 another time causes the ROI to change back to the ROI for both the mitral and atrial valves.

Figure 4:
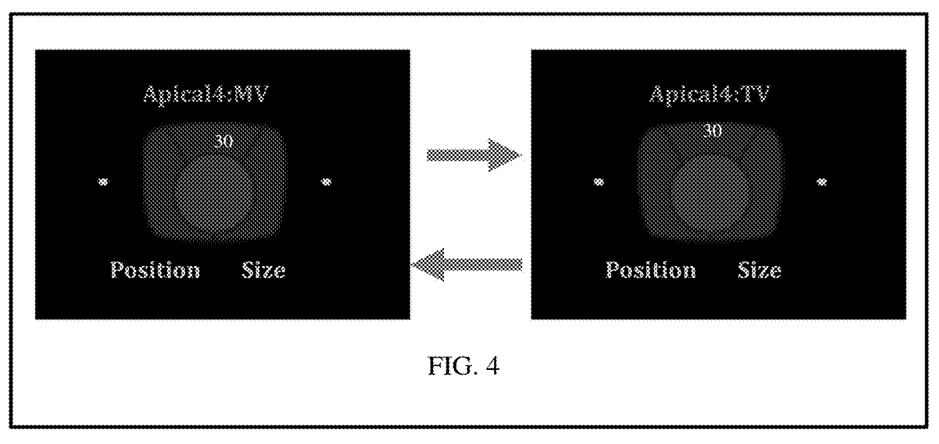
FIG. 4 illustrates an example of cycling through different anatomical locations for an apical four chamber view.

FIG. 4 shows an example corresponding to the apical four chamber view of FIGS. 2A and 2B. The button 30 is activated to place the ROI for imaging flow at the mitral valve. Activating the button 30 again causes the ROI to change to the tricuspid valve. Activating the button 30 yet again causes the ROI to change back to the mitral valve.

Figure 5A:
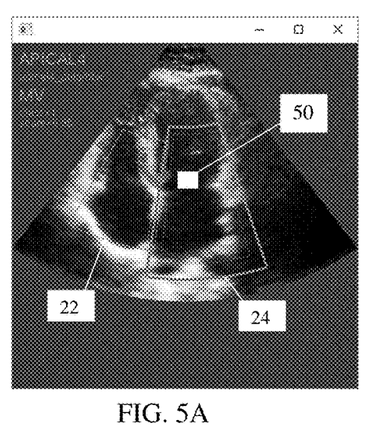
FIGS. 5A and 5B illustrate example Doppler gate locations available based on classification of a view as apical four chamber.
Figure 5B:
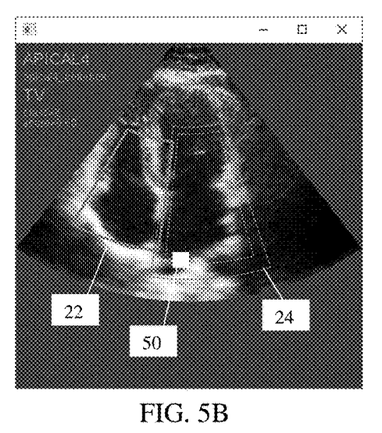

FIGS. 5A and 5B show an example for placement of a PW or Doppler gate 50 for the flow imaging. In one embodiment, the anatomical selection options assigned to the user interface element are gate locations. By activating the user interface element, the next gate location on the list of locations for the recognized view is used. In this apical four chamber view example, two gate locations are provided— the mitral valve and the pulmonic vein. The Doppler gate 50 is placed for the flow imaging by cycling through the anatomy list in response to use of the user input element.

In another embodiment, the PW or Doppler gate 50 positioning is tied to the ROI selection. The selection of the ROI 22, 24 also provides selection of a corresponding PW gate 50 location. The Doppler gate 50 is placed based on selection of anatomy for a flow ROI 22, 24 using the anatomy selection options. Automatic PW gate placement depends on the cardiac view with anatomical area selection dependent on the current color ROI position and its correspondence to detected anatomy. For example, use of the user interface element to select the ROI 24 over the mitral valve also places the PW gate 50 at the mitral valve. Further activation of the user interface element shifts the ROI to the ROI 22, which places the PW gate 50 at the pulmonic vein. In other embodiments, activation of the user input element may shift or change position of the PW gate 50 for a given ROI. For example, the list includes combinations of ROI and PW gate positions. Each activation moves to the next combination. In another embodiment, the Doppler gate is place first. When the user activates color (flow-mode), the flow ROI is positioned based on the selection of anatomy for the Doppler gate (i.e., based on the Doppler gate location). The PW gate placement guides the selection of a color ROI. If the user is operating in PW, then entry to color places the color ROI according to the view classifier while selecting the anatomy area most closely associated with the PW gate.

In act 15 of FIG. 1, the ultrasound scanner images based on the selected options from the behavior. In response to operation of the user interface element, the assigned action is performed by the ultrasound scanner. The user does not have to navigate to controls specific for sequencing through the actions (e.g., does not have to manually place the ROI and activate). Instead, the context-specific assigned options are used to automatically progress through the workflow.

In the cardiac example, flow imaging is performed. The flow imaging is for the ROI or PW gate as selected using context-based user interface. The selection both places the ROI or PW gate as well as activates the imaging. Alternatively, the placement occurs, and then subsequent operation of the user interface element or another element activates the imaging. The flow at a currently selected one of the anatomy selection options is imaged. The flow at other anatomy options may be imaged by changing the placement (i.e., activating the user interface element one or more times). Spectral Doppler (i.e., Doppler or PW mode) and/or color Doppler or flow-mode imaging is performed for the Doppler gate and/or flow ROI, respectively.

The flow imaging continues for any number of frames of ultrasound data or period. The detection and corresponding location of the ROI or PW gate may be updated during the flow imaging. As the transducer and/or patient shifts, the anatomy of interest may shift. By repeating the detection of anatomy, the location of the ROI or PW gate for the selected anatomy may automatically shift with the anatomy.

The classification of act 11 and assignment of act 13 may be repeated. For example, every time the user operates the user input element, the classification and assignment are repeated. If the view is the same based on the classification, then the assignment stays the same. If the view changes, then the assignment may change to the behavior (e.g., list of anatomy selection options) for the current or new view. For example, pressing "update" when in color initiates the view classification and object detection inference sequence. If the inferred cardiac view is unchanged, then object detection will select the next anatomical area in the sequence. If the view changes, then the anatomical area sequence starts back at the beginning for that view. The anatomy selection options assigned to the user input element vary with variance in the content as classified.

Once the ROI or PW gate is positioned or operation of the scanner changed, the ultrasound scanner performs the imaging, such as flow imaging. The imaging results in formation of one or more images. In the cardiac example, the images are combination B-mode with color mode and/or PW mode images. The generated image is displayed on a display device.

The ultrasound imaging is used for diagnosis, prognosis and/or treatment guidance. The use of classification-dependent user interface may avoid repetitive motions, simplify operation, and/or require a lesser extent of motion in operating the ultrasound scanner. The sonographer and patient benefit from the improvement as the total scan time may be less and more consistent imaging may be provided.

FIG. 7 shows one embodiment of a system 70 for an image classification-dependent user interface in ultrasound imaging. The system 70 is an ultrasound imaging system where the actions from one or more user inputs are assigned based on classification of the content in the imaging.

The system 70 is an ultrasound imager or scanner. In one embodiment, the ultrasound scanner is a medical diagnostic ultrasound imaging system. In alternative embodiments, the system 70 is a personal computer, workstation, PACS station, or other arrangement at a same location or distributed over a network for real-time or post acquisition imaging.

The system 70 implements the method of FIG. 1 or other methods. The system 70 includes a transmit beamformer 71, a transducer 72, a receive beamformer 73, an imager former 74, a display 75, an image processor 76, and a user input 77. Additional, different or fewer components may be provided. For example, a spatial filter, a scan converter, a mapping processor for setting dynamic range, and/or an amplifier for application of gain are provided. As another example, the user input 77 is part of the display 75, such as where a touch screen display is used.

The transmit beamformer 71 is an ultrasound transmitter, memory, pulser, analog circuit, digital circuit, or combinations thereof. The transmit beamformer 71 is configured to generate waveforms for a plurality of channels with different or relative amplitudes, delays, and/or phasing to focus a resulting beam at one or more depths. The waveforms are generated and applied to a transducer array with any timing or pulse repetition frequency.

The transmit beamformer 71 connects with the transducer 72, such as through a transmit/receive switch. Upon transmission of acoustic waves from the transducer 72 in response to the generated waves, one or more beams are formed during a given transmit event. The beams are for B-mode, color or flow-mode, PW mode, or other mode of imaging. Sector, Vector®, linear, or other scan formats may be used. The same region is scanned multiple times for generating a sequence of images or for quantification.

The transducer 72 is a 1-, 1.25-, 1.5-, 1.75- or 2-dimensional array of piezoelectric or capacitive membrane elements. The transducer 72 includes a plurality of elements for transducing between acoustic and electrical energies. For example, the transducer 72 is a one-dimensional PZT array with about 64-256 elements. As another example, the transducer 72 is a transesophageal echocardiography (TEE) array, a volume intracardiac echocardiography (ICE) array, or a trans-thoracic echo (TTE) array.

The transducer 72 is releasably connectable with the transmit beamformer 71 for converting electrical waveforms into acoustic waveforms, and with the receive beamformer 73 for converting acoustic echoes into electrical signals. The transducer 72 transmits the transmit beams where the waveforms have a frequency and are focused at a tissue region or location of interest in the patient. The acoustic waveforms are generated in response to applying the electrical waveforms to the transducer elements. The transducer 72 transmits acoustic energy and receives echoes. The receive signals are generated in response to ultrasound energy (echoes) impinging on the elements of the transducer 72.

The transducer 72 is a hand-held probe for use external to the patient. Alternatively, the transducer 72 is part of a probe for insertion within the patient. The transducer 72 may be positioned at various locations relative to the patient by the user and/or by a robotic arm.

The receive beamformer 73 includes a plurality of channels with amplifiers, delays, and/or phase rotators, and one or more summers. Each channel connects with one or more transducer elements. The receive beamformer 73 applies relative delays, phases, and/or apodization to form one or more receive beams in response to each transmission for detection. Dynamic focusing on receive may be provided. The receive beamformer 73 outputs data representing spatial locations using the received acoustic signals. Relative delays and/or phasing and summation of signals from different elements provide beamformation.

The receive beamformer 73 may include a filter, such as a filter for isolating information at a second harmonic or other frequency band relative to the transmit frequency band. Such information may more likely include desired tissue, contrast agent, and/or flow information. In another embodiment, the receive beamformer 73 includes a memory or buffer and a filter or adder. Two or more receive beams are combined to isolate information at a desired frequency band, such as a second harmonic, cubic fundamental, or another band. The fundamental frequency band may alternatively be used.

The receive beamformer 73 outputs beam summed data representing spatial locations. The beam summed data is in an I/O or RF format. Ultrasound signals or data are output.

The imager former 74 detects, such as detecting intensity, from the beamformed samples. Any detection may be used, such as B-mode, Doppler (erg, PW Doppler), and/or color or flow detection. The imager former 74 may or may not include a scan converter and/or spatial or temporal filters.

The user input 77 is a mouse, trackball, touchpad, touch screen, keyboard, buttons, sliders, knobs, and/or other input device. The user input 77 operates with the display 75 to provide a user interface generated by the imager processor 76.

The image processor 76 is a controller, general processor, application specific integrated circuit, field programmable gate array, graphics processing unit, or another processor to control the user interface and operation of the ultrasound system 70 based on classification of content of an image. The imager processor 76 includes or interacts with different components of the system 70 to control scanning and imaging. The imager processor 76 is configured by hardware, software, and/or firmware.

The imager processor 76 is configured to classify anatomy represented in ultrasound data. The content of one or more frames of ultrasound data are identified automatically or without user indication for the particular image.

The image processor 76 is configured to alter behavior of a user interface component based the classification of the anatomy such that different classification provides for different behavior of the same user interface component. The action or actions assigned to one or more buttons, keys, knobs, sliders, or other user interface component are different depending on the identified content. For example, different locations and/or orders of locations for ROI or PW gate positioning are assigned to a single user interface component. Different content results in a different list and/or order being assigned.

The image processor 76 is configured to receive selection of an anatomy area using the user interface component with the assigned behavior for the classification. The operation of the user interface component, such as a single button, activates the assigned action or actions. For example, operation of the single button cycles or sequences through different anatomical regions for the ROI or PW gate placement. The assigned list of anatomical regions of the anatomy of the patient represented in the image or frame of ultrasound data is used to sequence through different placements. The classification indicates the available placements, and the assigned user interface element allows selection of one of the available placements. For example, the location for a color Doppler ROI or a Doppler gate for PW Doppler imaging is selected by the user using the button.

The ultrasound system 70 is configured to image based on the selection of the anatomy area. The color mode, flow-mode, or PW mode flow imaging is performed for the selected ROI and/or PW gate location. The ROI and/or PW gate selected from available locations for the anatomical content of the image at a given time is used for imaging.

The display 75 is a CRT, LCD, monitor, plasma, projector, printer or other device for displaying an image or sequence of images. Any now known or later developed display 75 may be used. The display 75 displays a B-mode image, a flow-mode image, a PW image, or another image. The display 75 may display one or more images representing the ROI or PW gate placement as part of the user interface for selecting the anatomy of current interest.

The imager processor 76 and/or the ultrasound system 70 operate pursuant to instructions stored in a memory. The instructions configure the system for performance of the acts of FIG. 1. The instructions configure for operation by being loaded into a controller, by causing loading of a table of values (e.g., elasticity imaging sequence), and/or by being executed. The memory is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for flow imaging with an ultrasound scanner, the method comprising:
   scanning a patient with the ultrasound scanner;
   classifying, by the ultrasound scanner, content of an image from the scanning;
   assigning anatomy selection options to a user input element of the user interface, the anatomy selection options assigned based on the classified content, and the anatomy selection options comprising different anatomical parts of the content;
   for the flow imaging, placing a Doppler gate or color region of interest at a currently selected anatomy selection option in response to user input with the user input element, the user input selecting different anatomy using the anatomy selection options as assigned based on the classified content, and cycling through the anatomy selection options in response to repeated operation of the user input element, wherein a Doppler gate or color region of interest is placed at each anatomy selection option as the anatomy selection options are cycled through and flow is imaged at each anatomy selection option as the anatomy selection options are cycled through; and
   imaging flow at a currently selected one of the anatomy selection options with the Doppler gate or color region of interest as placed.

2. The method of claim 1 wherein classifying and assigning occur in real-time with the scanning.

3. The method of claim 1 wherein classifying further comprises identifying a view represented by the image.

4. The method of claim 3 wherein identifying the view further comprises identifying the view as one of apical four chamber, apical two chamber, parasternal long axis, and parasternal short axis.

5. The method of claim 1 wherein classifying further comprises classifying by application of a machine-learned model.

6. The method of claim 1 wherein assigning further comprises assigning an anatomy list as the anatomy selection options for anatomy of the content of the image, and wherein placing further comprises placing the color region of interest for the flow imaging by cycling through the anatomy list in response to use of the user input element.

7. The method of claim 1 wherein assigning further comprises assigning an anatomy list as the anatomy selection options for anatomy of the content of the image, and wherein placing further comprises placing the Doppler gate for the flow imaging by cycling through the anatomy list in response to use of the user input element.

8. The method of claim 1 wherein assigning further comprises assigning an anatomy list as the anatomy selection options for anatomy of the content of the image, and wherein placing further comprises placing the Doppler gate or the color region of interest based on selection for the Doppler gate or the color region of interest, respectively, using the anatomy selection options.

9. The method of claim 1 further comprising detecting locations of features of the content, and wherein assigning comprises including the locations of the features in the anatomy selection options.

10. The method of claim 1 wherein the user input element comprises a button, and wherein placing further comprises cycling through the anatomy selection options in response to operation of the button.

11. The method of claim 1 further comprising repeating the classifying and assigning in response to use of the user input element.

12. The method of claim 1 wherein assigning anatomy selection options to a user input element of the user interface further comprises a graphical representation of the anatomy selection options assigned based on the classified content.

13. The method of claim 1 wherein the user input element comprises a voice activation term, and wherein assigning further comprises assigning the anatomy selection options to the voice activation term.

14. A method for flow imaging with an ultrasound scanner, the method comprising:
   scanning, by the ultrasound scanner, a cardiac region of a patient;
   identifying, by the ultrasound scanner, a cardiac view in an image from the scanning;
   assigning a list of anatomical locations of the identified cardiac view to a single user input of the ultrasound scanner, the anatomical locations comprising a valve, a vein, a vessel, an artery, or a heart wall;
   selecting one of the anatomical locations in response to operation of the single user input, repeated operation of the single user input cycling through the anatomical locations; and
   for the flow imaging placing a Doppler gate or color region of interest at the currently selected one of the anatomical locations, wherein a Doppler gate or color region of interest is placed at each anatomical location as the anatomical locations are cycled through and flow is imaged at each anatomical location as the anatomical locations are cycled through.

15. The method of claim 14 wherein assigning further comprises assigning the list to a single button, and wherein selecting further comprises cycling through the list in response to repetitive operation of the single button.

16. The method of claim 14 wherein selecting further comprises selecting the Doppler gate or the flow color region of interest, and wherein flow imaging comprises spectral Doppler or color Doppler imaging for the Doppler gate or the flow color region of interest, respectively.

17. A system for flow imaging, the system comprising:
   An image processor configured to classify anatomy represented in ultrasound data, alter behavior of a user interface component based on the classification of the anatomy such that different classification provides for different behavior of the same user interface component, and receive selection of an anatomy area comprising one of different anatomical parts presented based on the classification using the user interface component with the behavior for the classification, repeated operation of the user interface component configured to cycle through anatomy areas comprising one of the different anatomical parts; and an ultrasound system configured to place a Doppler gate or color region of interest at a currently selected anatomy area to perform the flow imaging based on the selection of the anatomy area, the ultrasound system configured to place a Doppler gate or color region of interest at each anatomy area as the anatomy areas are cycled through and image flow at each anatomy area as the anatomy areas are cycled through.

18. The system of claim 17 wherein the user interface component further comprises a single button where the behavior comprises a list of anatomical regions of the anatomy, the anatomy area comprising one of the anatomical regions where the list is based on the classification and operation of the single button cycles through the list.

19. The system of claim 17 wherein the image processor is configured to receive the selection as the color region of interest for color Doppler or the Doppler gate for pulsed wave Doppler imaging.

\* \* \* \* \*